(12) United States Patent
Lee et al.

(10) Patent No.: US 9,084,672 B2
(45) Date of Patent: Jul. 21, 2015

(54) SELF-REGULATED ARTIFICIAL IRIS AND METHOD OF FABRICATING THE SAME

(71) Applicant: SNU R&DB FOUNDATION, Seoul (KR)

(72) Inventors: Sin Doo Lee, Seoul (KR); Jun Hee Na, Seoul (KR)

(73) Assignee: SNU R&DB Foundation, Seoul (KR)

( * ) Notice: Subject to any disclaimer, the term of this patent is extended or adjusted under 35 U.S.C. 154(b) by 102 days.

(21) Appl. No.: 13/751,828

(22) Filed: Jan. 28, 2013

(65) Prior Publication Data
US 2013/0297014 A1    Nov. 7, 2013

(30) Foreign Application Priority Data

May 7, 2012    (KR) .................. 10-2012-0047866

(51) Int. Cl.
| | | |
|---|---|---|
| *A61F 2/14* | (2006.01) | |
| *G02C 7/04* | (2006.01) | |
| *A61L 27/34* | (2006.01) | |
| *A61L 27/50* | (2006.01) | |

(52) U.S. Cl.
CPC . *A61F 2/14* (2013.01); *A61F 2/141* (2013.01); *A61L 27/34* (2013.01); *A61L 27/50* (2013.01); *G02C 7/046* (2013.01); *A61L 2430/16* (2013.01)

(58) Field of Classification Search
CPC ......... A61F 2/0059; A61F 2/14; A61F 2/141; G02B 5/23; G02C 7/047; G02C 7/102
USPC .................. 623/4.1; 351/159.24, 159.61
See application file for complete search history.

(56) References Cited

U.S. PATENT DOCUMENTS

| | | | |
|---|---|---|---|
| 5,108,427 A * | 4/1992 | Majercik et al. ............ 623/5.12 |
| 2004/0001181 A1* | 1/2004 | Kunzler et al. ............... 351/162 |
| 2008/0002147 A1* | 1/2008 | Haywood et al. ......... 351/160 R |
| 2010/0110521 A1* | 5/2010 | Kawaguchi et al. .......... 359/241 |

FOREIGN PATENT DOCUMENTS

| | | |
|---|---|---|
| JP | 04-029215 A | 1/1992 |
| JP | 2004-113792 A | 4/2004 |
| KR | 10-0729881 B1 | 6/2007 |
| WO | WO 2004/052631 A2 | 6/2004 |

* cited by examiner

*Primary Examiner* — Randy Shay
(74) *Attorney, Agent, or Firm* — Fenwick & West LLP

(57) ABSTRACT

The present disclosure provides an artificial iris prepared by forming a ring-shaped hydrophilic region on a biocompatible substrate, coating a curable material thereon and then coating a photoreactive material mimicking the iris frills through optical irradiation. The artificial iris may be implemented into the real human eye and is capable of regulating the intensity of the light reaching the retina through the pupil depending on the intensity of ambient light.

8 Claims, 8 Drawing Sheets

Artificial iris

Tunable transmitrance
(fixed pupil size($r_0$))

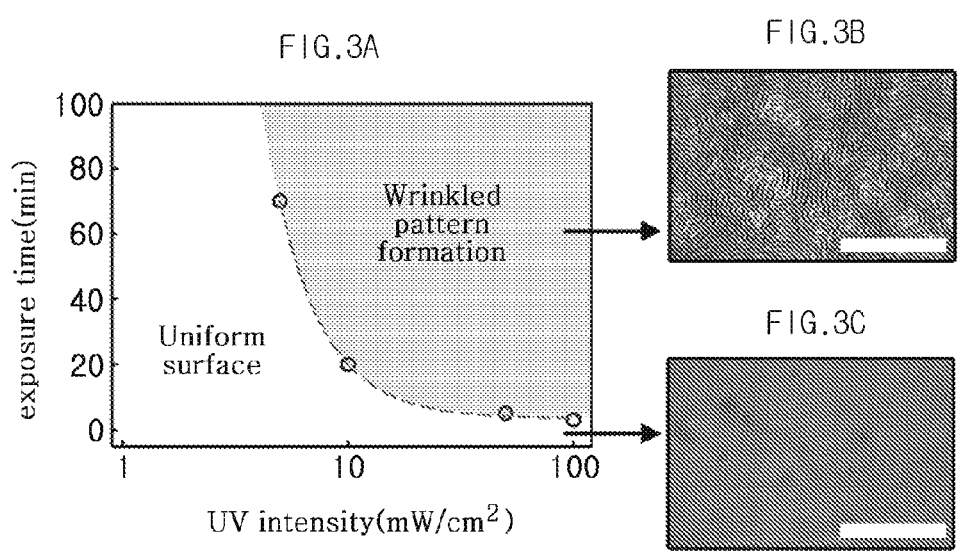

SELF-REGULATED ARTIFICIAL IRIS AND METHOD OF FABRICATING THE SAME

CROSS-REFERENCE TO RELATED APPLICATION

This application claims priority to Korean Patent Application No. 10-2012-0047866, filed on May 7, 2012, and all the benefits accruing therefrom under 35 U.S.C. §119, the contents of which in its entirety are herein incorporated by reference.

BACKGROUND

1. Field

The present disclosure relates to an artificial iris, more particularly to an artificial iris capable of self-regulating the transmittance of ambient light.

2. Description of the Related Art

The human eye is a very important organ responsible for vision. In particular, the iris, which regulates the amount of light reaching the retina through the pupil, is a critical element of the eye. Although the existing artificial irises have structures mimicking the iris frills, they exhibit poor transmittance regulating capability. And, although the most recent artificial iris technique adopts sensors and driving circuits for regulation of transmittance, practical implementation into the human eye is limited due to complexity and need of additional components. Accordingly, an artificial iris mimicking the real iris frills capable of self-regulating the transmittance of light without requiring a driving circuit is needed.

SUMMARY

To solve this problem, an artificial iris mimicking the real iris frills capable of self-regulating the transmittance of light without requiring a driving circuit is needed.

A self-regulated artificial iris according to an exemplary embodiment of the present disclosure may include: a substrate on which a ring-shaped hydrophilic region is formed; a curable material layer which is coated on the substrate and is cured; and a photoreactive material layer coated on the curable material layer.

The curable material layer may include radial surface wrinkles in a direction perpendicular to concentric circles.

The photoreactive material layer may include a photochromic material layer.

The ring may have an inner diameter of 4 mm and an outer diameter of 11 mm.

A method for fabricating a self-regulated artificial iris according to an exemplary embodiment of the present disclosure may include: forming a ring-shaped hydrophilic region on a substrate; coating a curable material on the hydrophilic region; curing the coated curable material; and coating a photoreactive material on the cured curable material.

The forming of the ring-shaped hydrophilic region may include: coating a hydrophobic material on the substrate; and etching the hydrophobic material using ultraviolet light or laser.

Also, the forming of the ring-shaped hydrophilic region may include soft lithography patterning.

The curing of the coated curable material may include forming radial surface wrinkles in a direction perpendicular to concentric circles through optical irradiation.

A light source with a wavelength of 140-800 nm may be used in the optical irradiation.

The photoreactive material may be a photochromic material.

In accordance with the present disclosure, an artificial iris capable of self-regulating transmittance and implementable to the human eye may be fabricated, overcoming the limitation of the existing artificial irises mimicking only the structural shapes.

Whereas the existing artificial irises require an external driving circuit for regulation of transmittance, the artificial iris according to an exemplary embodiment of the present disclosure is capable of self-regulating the transmittance of light incident on the human eye using the iris part mimicking iris frills. Further, since the fabrication process is simple, it may be practically implemented into the human eye. Unlike the existing artificial irises which mimic only the shape of the iris frills, the artificial iris according to an exemplary embodiment of the present disclosure is capable of self-regulating transmittance depending on the intensity of ambient light and is biocompatible and. In addition, it is implementable on the human eye since it may be fabricated on a flexible substrate.

BRIEF DESCRIPTION OF THE DRAWINGS

The above and other aspects, features and advantages of the disclosed exemplary embodiments will be more apparent from the following detailed description taken in conjunction with the accompanying drawings in which:

FIG. 3A is a graph showing wrinkle pattern formation depending on UV intensity and irradiation time and FIG. 3B and FIG. 3C show surface images;

DETAILED DESCRIPTION

Exemplary embodiments now will be described more fully hereinafter with reference to the accompanying drawings, in which exemplary embodiments are shown. The present disclosure may, however, be embodied in many different forms and should not be construed as limited to the exemplary embodiments set forth therein. Rather, these exemplary embodiments are provided so that the present disclosure will be thorough and complete, and will fully convey the scope of the present disclosure to those skilled in the art. In the description, details of well-known features and techniques may be omitted to avoid unnecessarily obscuring the presented embodiments.

The present disclosure is directed to providing an artificial iris capable of self-regulating the transmittance of ambient light, wherein a surface structure resembling the real iris frills and a photoreactive material whose transmittance changes reversibly depending on the intensity of the ambient light are used, and a method for fabricating same.

To achieve this, a ring-shaped hydrophilic region is formed on a biocompatible substrate and a curable material is coated on the hydrophilic region and then cured. Then, a photoreactive material is coated on the cured material to fabricate a self-regulated artificial iris.

Hereinafter, a method for fabricating an artificial iris including a wrinkle structure according to the present disclosure will be described in detail referring to the attached drawings.

Figure 1A:
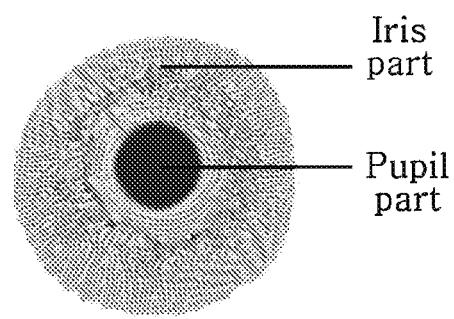
FIG. 1A shows a plan view and FIG. 1B shows a conceptual view of a self-regulated artificial iris according to an exemplary embodiment of the present disclosure wherein surface wrinkles are formed and a photoreactive material is coated.
Figure 1B:
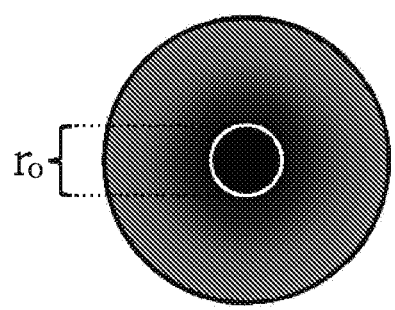

FIG. 1A shows a plan view and FIG. 1B shows a conceptual view of a self-regulated artificial iris according to an exemplary embodiment of the present disclosure wherein surface wrinkles are formed and a photoreactive material are coated. As seen from FIG. 1A, an artificial iris according to an exemplary embodiment of the present disclosure may be divided into an iris part mimicking the human iris and a pupil part where the pupil will be located. Referring to FIG. 1B, the self-regulated iris according to an exemplary embodiment of the present disclosure may adopt a photochemical reactivity regulation mechanism of self-regulating the transmittance of the artificial iris part with the pupil size fixed to that in a bright place, whereas the real human iris dynamically regulates the transmittance by controlling the size of the iris in response to the intensity of ambient light.

Figure 2A:
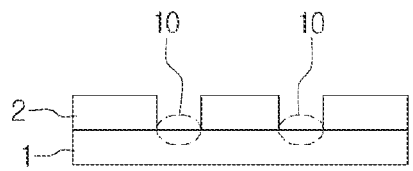
FIGS. 2A, 2B, and 2C illustrate a method for fabricating a self-regulated artificial iris according to an exemplary embodiment of the present disclosure.
Figure 2D:
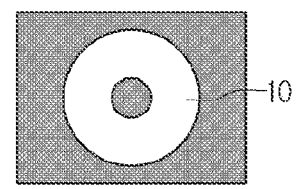
FIG. 2D shows the substrate of FIG. 2A seen from above.
Figure 2B:
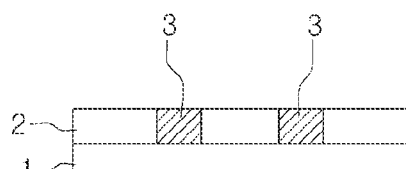
Figure 2E:
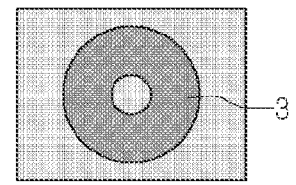
FIG. 2E shows the self-regulated artificial iris of FIG. 2B seen from above.
Figure 2C:
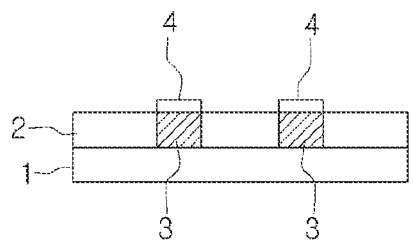

FIGS. 2A, 2B, and 2C illustrate a method for fabricating a self-regulated artificial iris according to an exemplary embodiment of the present disclosure.

Referring to FIG. 2A, a ring-shaped hydrophilic groove region 10 may be formed on a biocompatible, flexible substrate 1. FIG. 2D shows the substrate of FIG. 2A seen from above.

Specifically, the ring-shaped hydrophilic region 10 may be formed by etching using ultraviolet light or laser.

After coating a hydrophobic material 2 on the substrate 1 and positioning a photomask formed with a shape of the iris on the substrate, the hydrophobic material 2 may be selectively etched by irradiating ultraviolet light or laser so as to form the hydrophilic region 10 having a shape of the iris (ring). The hydrophilic region may be formed by irradiating ultraviolet light with an intensity of about 100 mW/cm2 for about 1 hour.

In an exemplary embodiment of the present disclosure, the ring-shaped hydrophilic region 10 may be formed by soft lithography patterning such as transfer printing. Specifically, a mold is prepared from a soft material by engraving a ring-shaped pattern. The mold is dip-coated to a hydrophobic material and the mold with the hydrophobic material attached is stamped on a substrate to form the ring-shaped hydrophilic region.

In an exemplary embodiment of the present disclosure, the hydrophobic material 2 may be a fluorine-based polymer material. The hydrophobic material has a contact angle of about 110° or greater whereas the etched portion has a contact angle of about 90° or smaller since the substrate is exposed. As a result, the hydrophilic region is formed. The ring-shaped hydrophilic region may have an inner diameter of about 4 mm and an outer diameter of about 11 mm.

Referring to FIG. 2B, a curable material 3 may be formed on the ring-shaped hydrophilic region 10 using a solution of a liquid crystal polymer material and then cured. FIG. 2E shows the self-regulated artificial iris of FIG. 2B seen from above.

The curable material 3 may be cured by irradiating ultraviolet light. As a result of the curing, uniform radial surface wrinkles may be formed in a direction perpendicular to circles concentric to and coplanar with the ring-shaped hydrophilic groove region 10. The wrinkles may be formed as the curable material is aligned radially at the hydrophilic/hydrophobic interface. The curable material may be a material including a photocurable or thermally curable component.

Figure 2F:
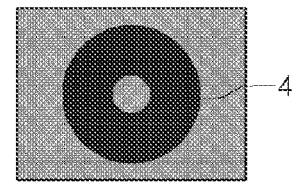
FIG. 2F shows the self-regulated artificial iris of FIG. 2C seen from above.

Referring to FIG. 2C, a transmittance-tunable material 4 may be coated on the curable material 3 having the wrinkles formed so as to enable the regulation of transmittance. FIG. 2F shows the self-regulated artificial iris of FIG. 2C seen from above. The transmittance-tunable material may be a photoreactive material and the photoreactive material may be a photochromic material whose transmittance is changeable depending on the intensity of ambient light.

FIG. 3A is a graph showing wrinkle pattern formation depending on light intensity and irradiation time and FIG. 3B and FIG. 3C show surface images.

FIG. 3A shows a result obtained by using a liquid crystal polymer material (RMS03-001C, Merck) as the curable material and irradiating ultraviolet light with a wavelength of about 365 nm. A wrinkle pattern may be formed when ultraviolet light of about 50 mW/cm2 in intensity is irradiated for 3 minutes or longer, as shown in FIG. 3B. The wrinkle pattern will not be formed when either the UV intensity is too low or the irradiation time is too short, as shown in FIG. 3C. The wrinkle pattern as shown in FIG. 3B may be formed using a light source with a wavelength of 140-800 nm. The result shown in FIG. 3A shows that not only the total energy of ultraviolet light but also the intensity of the ultraviolet light is important to form the surface wrinkles.

Figure 4A:
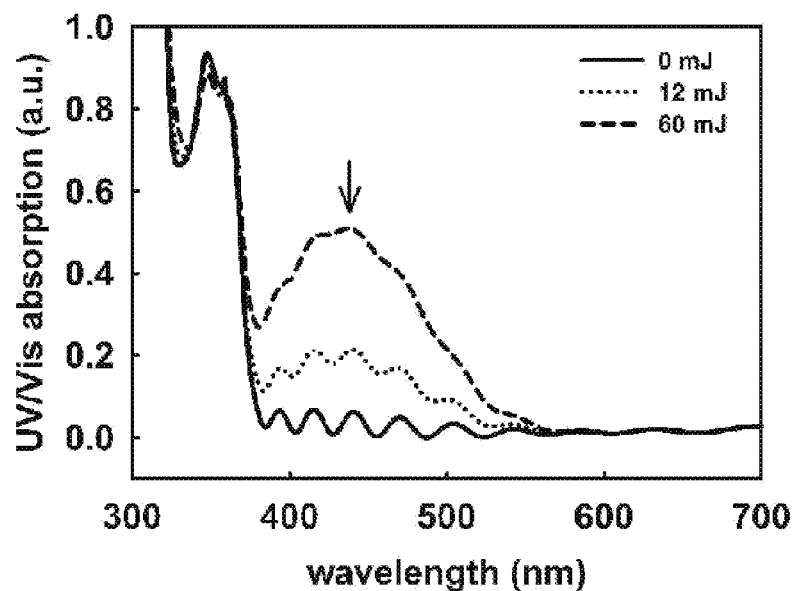
FIGS. 4A, 4B, 4C, and 4D show absorption of ultraviolet light and visible light by a photoreactive material according to an exemplary embodiment of the present disclosure.
Figure 4B:
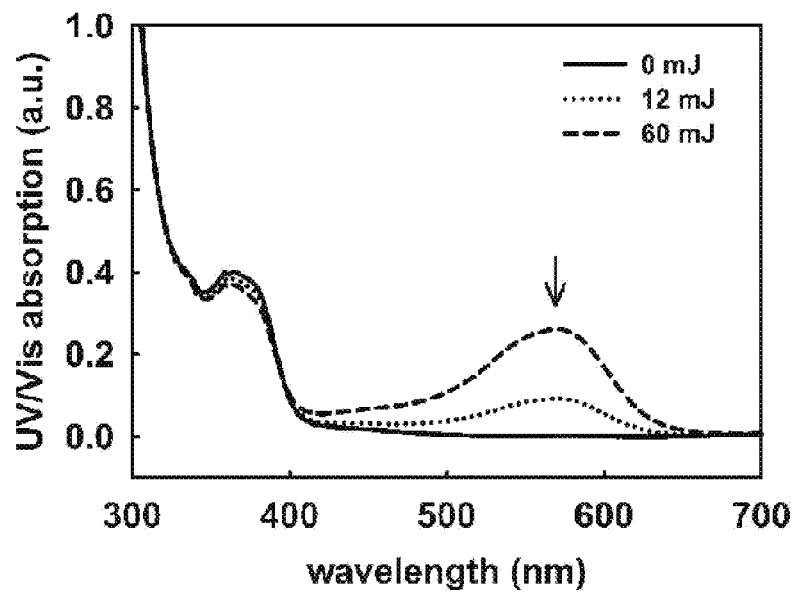
Figure 4C:
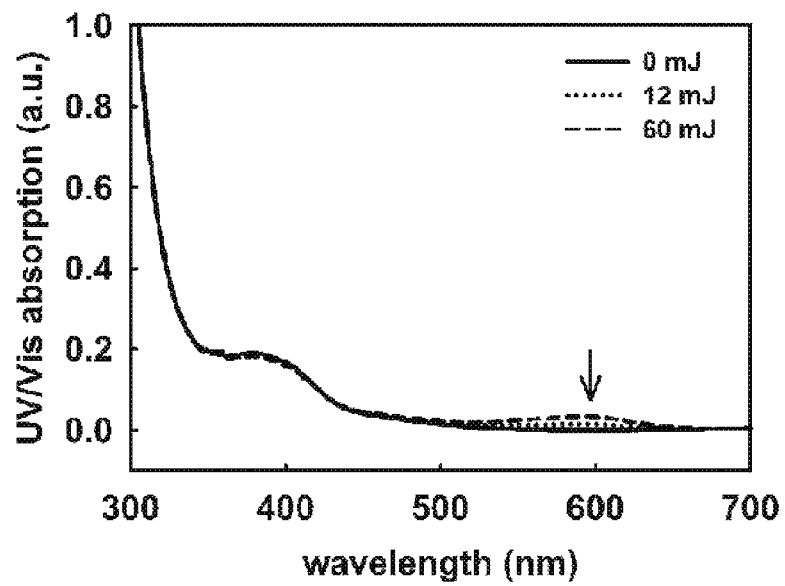
Figure 4D:
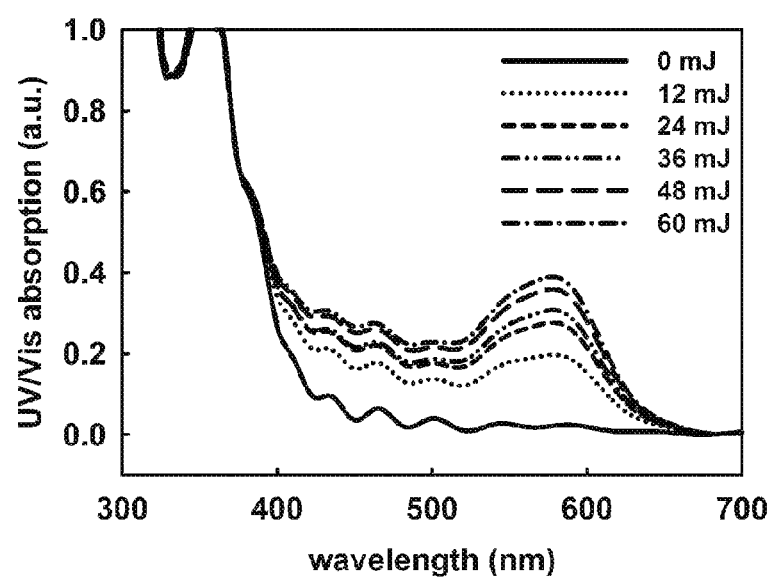

FIGS. 4A, 4B, 4C, and 4D show absorption of ultraviolet light and visible light by a photoreactive material according to an exemplary embodiment of the present disclosure. It can be seen that absorption increases and transmittance decreases relatively as the intensity of ambient light increases, which is typical of the spiropyran-based photoreactive material. FIGS. 4A, 4B, and 4C show the inherent absorption wavelengths of three photoreactive materials available from Nano I&C: D-Shine Photochromic-Blue (a), D-Shine Photochromic-Yellow (b) and D-Shine Photochromic-Violet (c), respectively. FIG. 4D shows a result for the three dyes blended with a mixing ratio of 2:1:1. Whereas the real human iris physically blocks ambient light by regulating the size of the iris, the artificial iris according to an exemplary embodiment of the present disclosure may be made to absorb light in the whole visible rage by mixing the three photoreactive materials with an appropriate ratio, as shown in FIG. 4D.

Figure 5:
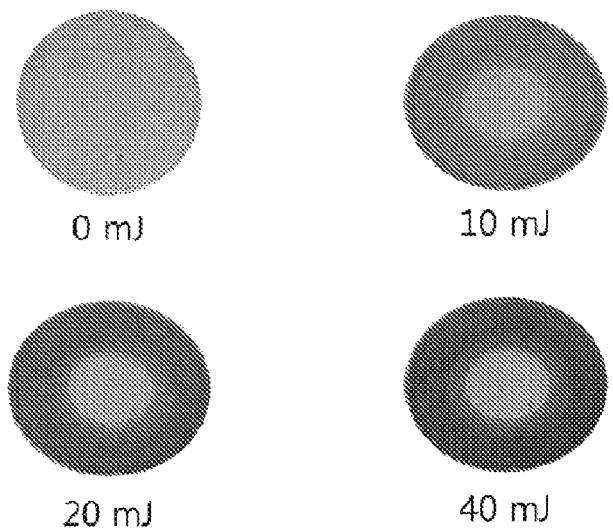
FIG. 5 shows change in transmittance of an artificial iris according to an exemplary embodiment of the present disclosure depending on the intensity of ambient light.

FIG. 5 shows change in the transmittance of the artificial iris according to an exemplary embodiment of the present disclosure depending on the intensity of ambient light. Referring to FIG. 5, when ultraviolet light of 365 nm wavelength is irradiated from an external light source for 0.4 second with an intensity of 0 mJ, 10 mJ, 20 mJ and 40 mJ, the color of the iris part becomes darker due to increased absorption. In other words, transmittance decreases as the intensity of ambient light increases.

Figure 6:
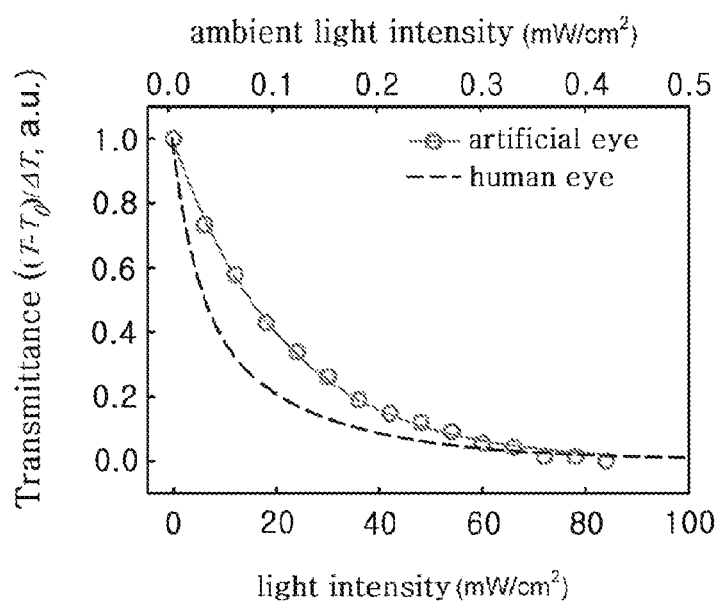
FIG. 6 shows transmittance of the artificial iris according to an exemplary embodiment of the present disclosure shown in FIG. 5 as a function of the intensity of ambient light.

FIG. 6 shows the transmittance of the artificial iris according to an exemplary embodiment of the present disclosure shown in FIG. 5 as a function of the intensity of ambient light. As seen from the graph, the artificial iris according to the present disclosure exhibits a transmittance behavior very similar that of the real human eye. The slight difference in transmittance may be minimized through optimization of the photoreactive material.

Figure 7:
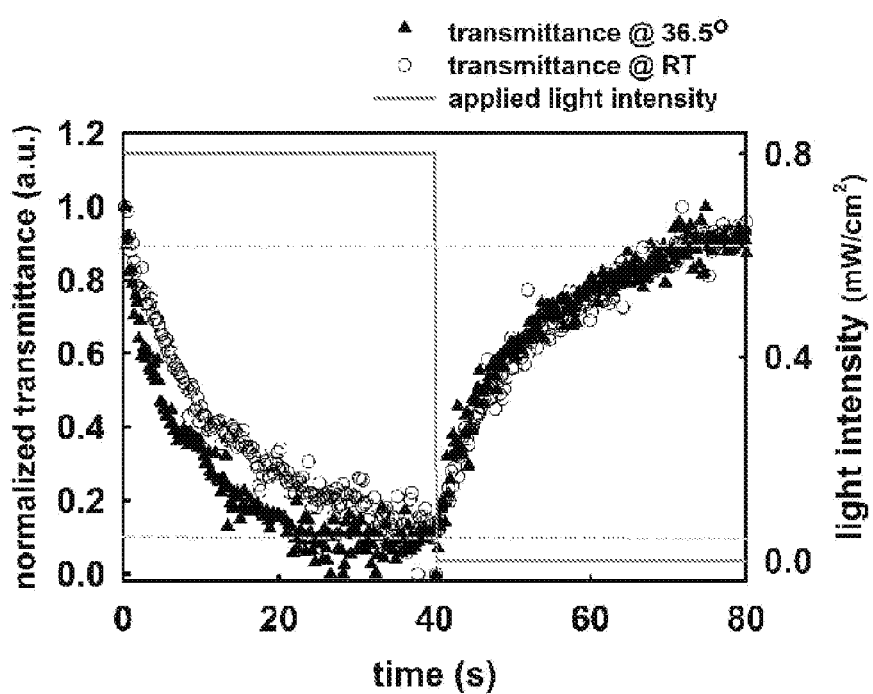
FIG. 7 shows change in dynamic transmittance of the artificial iris according to an exemplary embodiment of the present disclosure shown in FIG. 6 in the presence and absence of ambient light.

FIG. 7 shows change in the dynamic transmittance of the artificial iris according to an exemplary embodiment of the present disclosure shown in FIG. 6 in the presence and absence of ambient light. The change in transmittance at room temperature and human body temperature is shown in FIG. 7. The x-axis in FIG. 7 represents time. An external light (ultraviolet light) source with an intensity of 0.8 mW/cm2 is turned on until 40 seconds (on-state) and is turned off after 40 seconds (off-state). It can be seen that the transmittance decreases with time in the on-state and increases with time in the off-state, returning to the original state. This means that the transmittance may be regulated reversibly depending on the intensity of ambient light. The result of measuring dynamic transmittance at room temperature and the body temperature of 36.5° C. reveals that the decrease of transmittance in the state where the external light source is turned on is slightly dependent on temperature, but the increase of transmittance in the state where the external light source is turned off is almost independent of temperature. This is due to the inherent photochemical change of the photoreactive material. The temperature dependency may be enhanced or reduced by selecting appropriate materials. Likewise, the response rate of dynamic transmittance to the ambient light may be tuned.

Figure 8:
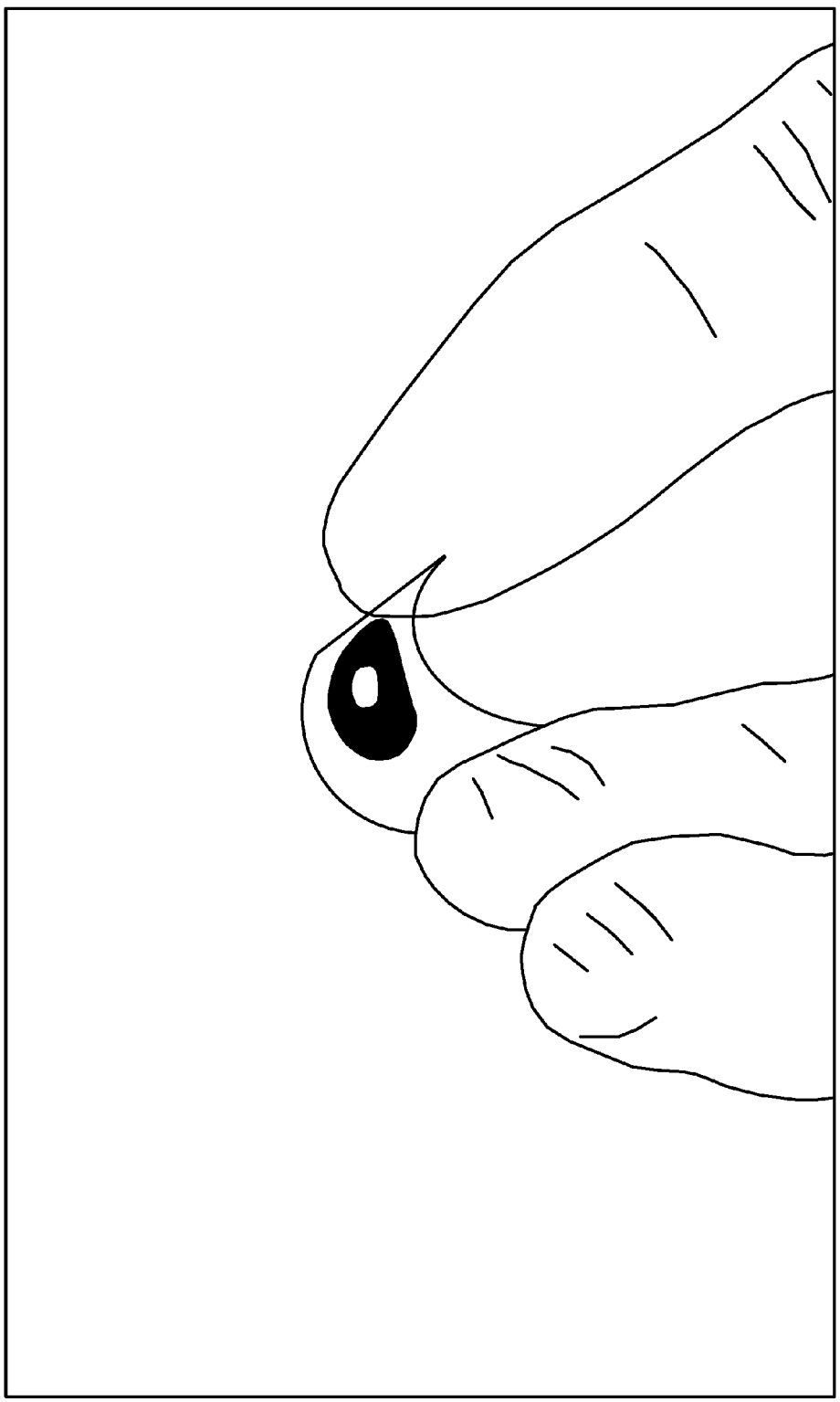
FIG. 8 shows a photographic image of an artificial iris according to an exemplary embodiment of the present disclosure fabricated on a flexible substrate.

FIG. 8 shows a photographic image of an artificial iris according to an exemplary embodiment of the present disclosure fabricated on a flexible substrate. For the artificial iris of the present disclosure to be implemented into the human eye, the unnecessary part should be removed from the substrate and use of a flexible substrate is indispensable. In an exemplary embodiment of the present disclosure, polyethersulfone (PES) may be as for the substrate. An artificial iris may be fabricated on a PES substrate according to the procedure illustrated in FIG. 2.

Those skilled in the art will appreciate that the hydrophobic material, the photoreactive material and the curable material may be coated by spin coating or dip coating. While the exemplary embodiments have been shown and described, it will be understood by those skilled in the art that various changes in form and details may be made thereto without departing from the spirit and scope of the present disclosure as defined by the appended claims. In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A self-regulated artificial iris comprising:
    a substrate on which a ring-shaped hydrophilic groove region is formed;
    a curable material layer which is coated on the ring-shaped hydrophilic groove region and is cured, the curable material layer comprising radial surface wrinkles in a direction perpendicular to circles concentric to and coplanar the ring-shaped hydrophilic groove region; and
    a photoreactive material layer coated on the curable material layer.

2. The self-regulated artificial iris according to claim 1, wherein the photoreactive material layer comprises a photochromic material layer.

3. The self-regulated artificial iris according to claim 1, wherein the ring-shaped hydrophilic groove region has an inner diameter of 4 mm and an outer diameter of 11 mm.

4. A method for fabricating a self-regulated artificial iris, comprising:
    forming a ring-shaped hydrophilic groove region on a substrate;
    coating a curable material on the hydrophilic groove region;
    curing the coated curable material so as to form radial surface wrinkles in a direction perpendicular to circles concentric to and coplanar with the ring-shaped hydrophilic groove region; and
    coating a photoreactive material on the cured curable material.

5. The method for fabricating a self-regulated artificial iris according to claim 4, wherein said forming the ring-shaped hydrophilic groove region comprises:
    coating a hydrophobic material on the substrate; and
    etching the hydrophobic material using ultraviolet light or laser.

6. The method for fabricating a self-regulated artificial iris according to claim 4, wherein said forming the ring-shaped hydrophilic groove region comprises soft lithography patterning.

7. The method for fabricating a self-regulated artificial iris according to claim 4, wherein a light source with a wavelength of 140-800 nm is used in the optical irradiation.

8. The method for fabricating a self-regulated artificial iris according to claim 4, wherein the photoreactive material is a photochromic material.

* * * * *